(12) United States Patent
Ancel et al.

(10) Patent No.: US 6,867,307 B2
(45) Date of Patent: Mar. 15, 2005

(54) INTERMEDIATES FOR USE IN THE PREPARATION OF VITAMIN E

(75) Inventors: Jean-Erick Ancel, Saint Genis Laval (FR); Pierre Meilland, Chaponost (FR)

(73) Assignee: Adisseo France S.A.S., Antony (FR)

( * ) Notice: Subject to any disclaimer, the term of this patent is extended or adjusted under 35 U.S.C. 154(b) by 0 days.

(21) Appl. No.: 10/343,129

(22) PCT Filed: Jul. 12, 2001

(86) PCT No.: PCT/EP01/09867

§ 371 (c)(1),
(2), (4) Date: Mar. 18, 2003

(87) PCT Pub. No.: WO02/14301

PCT Pub. Date: Feb. 21, 2002

(65) Prior Publication Data

US 2003/0166950 A1 Sep. 4, 2003

(30) Foreign Application Priority Data

Aug. 11, 2000 (EP) ............................................. 0017200

(51) Int. Cl.[7] ....................... C07D 311/04; C07C 45/00; C07C 61/00; C07C 211/00
(52) U.S. Cl. ....................... 549/408; 549/411; 564/502; 564/505; 564/506; 564/508; 564/569; 568/300; 568/386; 568/403; 568/404; 568/405; 568/579; 568/687; 568/689
(58) Field of Search ................................ 549/408, 411; 568/405, 403, 404, 687, 689, 383, 386, 300, 579; 564/509, 502, 505, 506, 508

(56) References Cited

FOREIGN PATENT DOCUMENTS

EP         0 544 588 A        6/1993

OTHER PUBLICATIONS

Liu et al., "The preparation and utilization of 2–ethylallyl alcohol dianions in alpha–alkylidene lactone synthesis", Synth. Commun., vol. 23, No. 10, 1993, pp. 1437–1442. XP000973211.
Mikami et al., "Catalytic Asymmetric Glyoxylate–Ene Reaction: A Practical Access to alpha–Hydroxy Esters in High Enantiomeric Purities", J. Amer. Chem. Soc., vol. 112, No. 10, 1990. pp. 3949–3954. XP000944681.

Whitesell et al , "Asymmetric induction in the ene reaction of glyoxylate esters of 8–phenylmenthol" TETRAHEDRON, vol. 42, No. 11, 1986. pp. 2993–3002. XP000941835.

Girodeau et al., "The Lysine Pathway as a Target for a New Genera of Synthetic Antibacterial Antibiotics?" J. Med. Chem., vol. 29, No. 6, 1986. pp. 1023–1030, XP000941834.

Ellis et al., "Homogeneous catalysis. Use of a ruthenium (II) complex for catalyzing the ene reaction" Chem. Commun., vol. 12, 1998, pp. 1311–1312. XP000973106.

Agourdias et al., "Syntheses of protected vinylic amino acids by intermolecular Lewis acid catalyzed ene reactions" Tetrahedron Lett., vol. 26. No. 26, 1985, pp. 3115–3118. XP000973036.

Sugimura et al., "A formation of optically active oxetanes from sugars by boron trifluroide catalyzed '2+2!cycloaddition reaction" Tetrahedron Lett., vol. 30. No. 12. 1989, pp. 1571–1574, XP000973008.

Benner et al., "Lewis Acid Catalysis of the Ene Addition of Chloral and Bromal to Olefins: Product Studies" J. Chem. Soc. Perkin Trans. I. No. 3, 1984.pp. 291–313. XP000972997.

Brimble et al., "Synthesis of (E)–1–bromo–3–ethyl–3–pentene" Synth. Commun., vol. 26, No. 2. 1996. pp. 243–251, XP000972981.

Mukaiyama et al., "The Addition Reaction of Acetals (Aldehydes) to Simple Olefins by the Use of a New Catalyst System" Chem. Lett. 1989. pp. 1277–1280 XP000972988.

Quian et al., "Glyoxylate–Ene Reaction Catalyzed by Ln (OTf)3" Tetrahedron Lett., vol. 38. No. 38. 1997. pp. 6721–6724. XP004089590.

Paul et al., "Recherches sur les acetals. II.—Formation d'ethers de diols–1–3 et d'alcohols ethyleniques par condensation des acetals avec les carbures ethyleniques." Bull. Soc. Chim. Fr., 1951. pp. 125–129. XP000944833.

*Primary Examiner*—Ceila Chang
*Assistant Examiner*—Raymond Covington
(74) *Attorney, Agent, or Firm*—Oliff & Berridge, PLC

(57) ABSTRACT

Intermediate compounds which can be used in the preparation of phytone and Vitamin E, a process for the preparation thereof, and a process for the preparation of phytone and Vitamin E from these intermediate compounds.

26 Claims, No Drawings

INTERMEDIATES FOR USE IN THE PREPARATION OF VITAMIN E

The present invention relates to a process for the preparation of intermediate compounds useful in the preparation of phytone and/or Vitamin E.

Vitamin E has been prepared chemically for a long time using many various processes. In general, this vitamin is prepared from an intermediate compound. European Patent 0544588 discloses a process for the production of Vitamin E through the condensation of a polyunsaturated allyl alcohol derivative. U.S. Pat. No. 3,867,408 discloses the preparation of novel ketal compounds which may be used in the preparation of phytone which in turn is an intermediate in the production of Vitamin E.

We have now found a new process for the preparation of certain beta olefinic compounds which can be used to synthesise phytone and in some cases which can be used to synthesise vitamin E directly from this intermediate.

Accordingly, the present invention provides a process for the preparation of a compound of general formula (I)

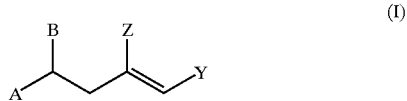

(I)

wherein A is a $C_1$ to $C_{20}$ hydrocarbon, Y and Z independently represent a $C_1$ to $C_{20}$ hydrocarbon which may contain an oxygenated functional group, and B represents $OR^1$ or $NHR^1$ where $R^1$ is hydrogen or a $C_1$ to $C_6$ hydrocarbon, which process comprises reacting, in the presence of a Lewis acid catalyst, a compound of the general formula (II)

(II)

wherein Y and Z are as herein before defined with a compound of the general formula (III) or a compound of general formula (IV)

(III)

(IV)

wherein A, B and R are as hereinbefore defined and R is hydrogen or a $C_1$ to $C_6$ hydrocarbon.

Certain compounds of general formula (I) are novel and as such also form another aspect of this invention.

The process of the present invention comprises the catalytic reaction between a compound of general formula (II) and a compound of general formula (III) or general formula (IV). With regard to the compound of general formula (II), Y and Z represent a $C_1$ to $C_{20}$ hydrocarbon which may contain an oxygenated functional group. The hydrocarbon group may be linear, cyclic, aromatic or aliphatic, substituted or unsubstituted. Where Z is a hydrocarbon, the preferred hydrocarbon is a linear aliphatic hydrocarbon, especially methyl. Compounds of general formula (II) suitable for use in the process of the present invention include 6-methyl-6-heptene-2-one; 2-methyl-1-heptene; 2,6,10,14 tetra methyl pentadec-1-ene, 6-acetoxy 2,5,7,8-tetramethyl 2-[(4-methyl pent-4-ene)-1 yl]chromene and 6-acetoxy 2,5, 7,8-tetramethyl 2-[(4-methyl pent-4-ene)-1 yl]chromane. The particularly preferred compounds of general formula (II) are 6-methyl-6-heptene-2-one; 6-acetoxy 2,5,7,8-tetramethyl 2-[(4-methyl pent-4-ene)-1 yl]chromene and acetoxy 2,5,7,8-tetramethyl 2-[(4-methyl pent-4-ene)-1 yl]chromane.

With regard to compounds of general formula (III), A represents a $C_1$ to $C_{20}$ hydrocarbon. The hydrocarbon may be linear or cyclic, substituted or unsubstituted and may be saturated or unsaturated. Preferably, A is a linerar aliphataic hydrocarbon, especially mathyl. B represents $OR^1$ or $NR^1$ where $R^1$ is a $C_1$ to $C_6$ aliphatic linear or cyclic hydrocarbon or a $C_6$ aromatic hydrocarbon. Compounds of general formula (III) particularly suitable for the process of the present invention include 3 methyl butanal; imines of 3-methyl butanal; 3,6-dimethyl octanal; imines of 3,6-dimethyl octanal; citral and imines of citral. By imine is meant methyl, ethyl, propyl, isopropyl, butyl, isobutyl, tertiary butyl, phenyl, tosyl and benzyl imines, prepared according to known methods.

With regard to compounds of general formula (IV), A represents a $C_1$ to $C_{20}$ hydrocarbon. The hydrocarbon may be linear or cyclic, substituted or unsubstituted and may be saturated or unsaturated and R is a $C_1$ to $C_6$ aliphatic linear or cyclic hydrocarbon or a $C_6$ aromatic hydrocarbon. Compounds of general formula (IV) particularly suitable for the process of the present invention include acetals of citral; acetals of 3-methyl butanal; acetals of 3,6-dimethyl octanal, The particularly preferred compound is 3,6-dimethyl octanal, 3-methyl butanal, and their acetals. By acetals, it is meant methyl, ethyl, isopropyl acetals and glycol prepared according to known methods.

The mole ratio of compound of general formula (II) to compound of general formula (III or IV) is suitably from 0.2:1 to 5:1, preferably from 0.5:1 to 2:1.

The process of the present invention is carried out in the presence of a Lewis acid. Suitable Lewis acids include compounds of the general formula M(L)n wherein M represents aluminium, iron, magnesium, scandium, ytterbium, zinc, titanium, silicium and bismuth; L represents a halide, $CF_3SO_3$, $(CF_3SO_2)_2N$, $ClO_4$ or a $C_1$ to $C_4$ alkyl, and n corresponds to the electronic valency of M and suitably is from 1 to 4. Alternatively, the Lewis acid may be a hydride compounds having the general formula A-H wherein A represents $CF_3SO_3$ or $(CF_3SO_2)_2N$.

In particular, Lewis acids according to the aforementioned definitions suitable for use in the process of the present invention include the metal chloride, for example the chloride of aluminium, iron, bismuth, zinc, magnesium, titanium, scandium and yttrium, trifluoromethane sulphonates of scandium, ytterbium, iron and aluminium; trifluoromethane sulphonic amide or the corresponding metal salt of scandium, ytterbium, iron and aluminium; and trifluoromethane sulphonic acid. The preferred Lewis acid is iron trichloride. The amount of catalyst used in the process is suitably from 0.001 to 5 molar equivalents, preferably from 0.02 to 2.5 molar equivalents.

The process of the present invention may be carried out in the presence of a base. Suitable bases may be chosen from aromatic amines, for example pyridine and 2,6, dimethyl pyridine; or aliphatic amines, especially tertiary amines, for example triethyl amine and di-isopropyl ethyl amine; or an inorganic carbonate, especially a carbonate of Group I or Group II of the Periodic Table, for example carbonates of sodium, potassium, calcium and magnesium. The preferred base is pyridine. The amount of base used in the process may be from 0 to 1 molar equivalent, preferably from 0.1 to 0.5 molar equivalent.

The reaction may be carried out in the presence of an organic solvent. Suitable solvents include chlorinated solvents such as dichloromethane, chloroform or chlorobenzene; aromatic solvents, for example toluen eand xylene; ether such as tetrahydrofuran, diethyl ether and isopropyl ether; nitrile solvents such as acetonitrile, proponitrile, and benzonitrile and nitro solvents such as nitromethane and nitroethane. The amount of solvent present in the reaction system is suitably from 0 to 100, preferably from 2 to 10 mass equivalents.

The process may be carried out at a temperature from minus 80 to plus 150° C., preferably from minus 50 to plus 25° C. and under atmospheric or elevated pressure. Preferably, the reaction is carried out under atmospheric pressure.

The process of the present invention may be carried out for a period of time from 30 minutes to 24 hours, preferably from 30 minutes to 6 hours under the aforementioned reaction conditions in order to facilitate complete reaction of compounds of general formula (II) or (III).

Certain compounds of general formula (I) are novel and as such form another aspect of the present invention. In particular compounds of formula V, VI, VII and VIII are novel compounds.

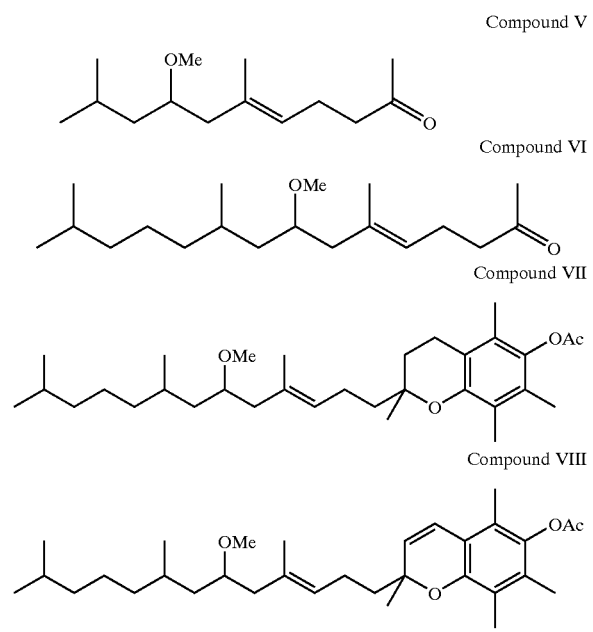

Compound V

Compound VI

Compound VII

Compound VIII

The compounds of general formula (I), obtained by the process of the present invention, are particularly suitable for use as starting materials in the synthesis of phytone and/or Vitamin E. Thus, according to another aspect of the present invention there is provided a process for the preparation of phytone and/or Vitamin E, which comprises the hydrogenolysis of the compound of general formula (I).

In a specific embodiment of this synthesis, Vitamin E may be obtained when the starting material is selected from compound (VII) or (VIII), where Y is a hydrocarbon containing a chromane or chromene moiety, as hereinbefore defined and phytone may be obtained when the starting material is selected from compound (V) or (VI), where Y is a linear $C_5$ ketone.

The hydrogenolysis stage of the process may be carried out in the presence of hydrogen gas and in the presence of a metal or metal salt. Suitable metals and metal salts include Raney nickel (a nickel/aluminium alloy) optionally in the presence of iron, mangenese, cobalt, copper, zinc or chromium; zinc in the presence of acetic acid; stannous chloride; and molybdenum (III) salts. The reaction may also be carried out in the pressence of palladium or platinum which may be supported on an suitable inert support such as charcoal. The hydrogenolysis is preferably carried out in the presence of palladium on an inert support such as on charcoal. The amount of metal or metal salt employed is generally from 0.01 to 3 molar equivalents, preferably from 0.05 to 2 molar equivalents.

The reaction may be carried out in the presence of a solvent which may be selected from an organic acid such as acetic acid; ethers; and aromatic hydrocarbons. The preferred solvents are acetic acid and toluene. The amount of solvent is suitably between 0 and 20 weight equivalents. The reaction may also be carried out in the presence of a inorganic acid, for example HCl or sulphonic acid. The amount of inorganic acid suitably is from 0 to 1 equivalents, preferably from 0.1 to 0.5 equivalents.

The reaction temperature may be from 20° C. to 150° C., preferably from 20° C. to 90° C. and under a pressure of 1 to 50 bars, preferably 1 to 10 bars.

The present invention will now be illustrated with reference to the following examples:

Examples 1 to 6 are directed to the production of the intermediate compounds, Examples 7 is directed to the production of a phytone intermediate and Examples 8 is directed to the production of Vitamin E.

In the following examples Tf represents $F_3CSO_2$.

EXAMPLE 1

The reaction, as detailed below was carried out in the presence of dichloromethane solvent using various Lewis acid catalysts and under conditions as indicated in Table 1

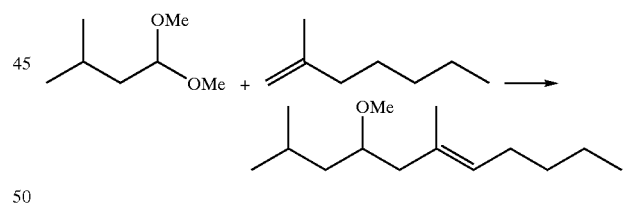

Eqimolar quantities of the two reactants were added under an inert atmosphere to the reactor containing the catalyst. The reaction was left to proceed for two hours before adding aqueous saturated sodium hydrogen carbonate magnesium sulphate, filtered and concentrated. The product was isolated by chromatography on silica gel or filtrated in crude solution after concentration of. The resulting product was extracted with ether, washed with water and dried using the solvent. The results are given in Table 1.

TABLE 1

| Catalyst and Amount | Temperature of Reaction (° C.) | Yield of Product (%) |
|---|---|---|
| 2.5 eq EtAlCl$_2$ | −30 | 85 |
| 5% Tf$_2$NH | 0 | 58 |

TABLE 1-continued

| Catalyst and Amount | Temperature of Reaction (° C.) | Yield of Product (%) |
|---|---|---|
| 5% Al(NTf$_2$)$_3$ | 0 | 15 |
| idem +5% pyridine | 20 | 50 |
| 5% Yb(NTf$_2$)$_3$ | 0 | 5 |
| 5% Yb(NTf$_2$)$_3$ | 20 | 70 |
| 5% Yb(OTf)$_3$ | 20 | 35 |
| 5% Al(OTf)$_3$ | 20 | 40 |
| 5% AlCl$_3$ | 20 | 15 |
| 5% FeCl$_3$ | 20 | 74 |
| 5% BiCl$_3$ | 20 | 30 |
| 5% ZnCl$_2$ | 20 | 5 |
| 5% TfOH | 20 | 30 |
| 5% TiCl$_4$ | 20 | 5 |

EXAMPLE 2

The reaction, as detailed below was carried out in the presence of dichloromethane solvent at 0° C.

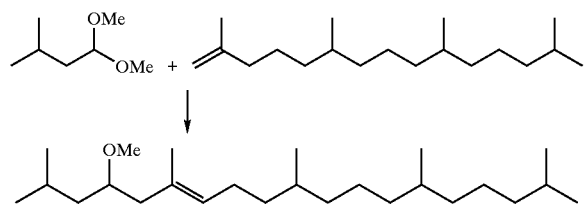

An equimolar mixture of 2,6,10,14 tetra methyl penta dec-1-ene (532 mg) and acetal (302 mg) was added under an inert atmosphere to the reactor containing 28 mg (0.049 equivalent) of (F3CSO$_2$)$_2$NH catalyst. The reaction was carried out for 2 hours at 0° C. and then 2 hours at 20° C. prior to the addition of aqueous saturated sodium hydrogen carbonate. The resulting product was extracted with ether, washed with water and dried using magnesium sulphate, filtered and concentrated. The product was isolated by chromatography on silica gel or filtrated in crude solution after concentration of the solvent. A yield of 54% was obtained after purification.

EXAMPLE 3

The procedure of Example 1 was repeated using the reactants as detailed in the reaction scheme below.

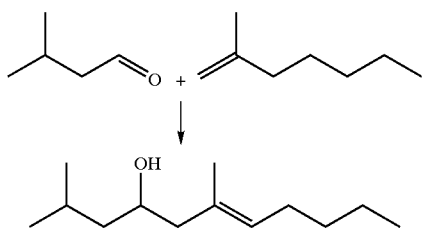

The reaction conditions, catalysts used and the resulting yields are given in Table 2 below.

TABLE 2

| Catalyst and Amount | Temperature of Reaction (° C.) | Yield of Product (%) |
|---|---|---|
| 5% Yb(NTf$_2$)$_3$ | 20 | 70 |
| 5% Al(NTf$_2$)$_3$ | 20 | 60 |
| 5% Al(OTf)$_3$ | 20 | 53 |
| 2.5 eq EtAlCl$_2$ | −15 | 5 |

EXAMPLE 4

The procedure of Example 1 was repeated using the reactants as detailed in the reaction scheme below.

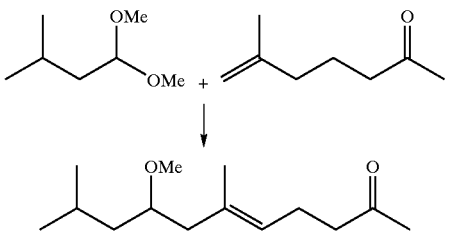

The reaction conditions, catalysts used and the resulting yields are given in Table 3 below.

TABLE 3

| Catalyst and Amount | Temperature of Reaction (° C.) | Yield of Product (%) |
|---|---|---|
| 2.5 eq EtAlCl$_2$ | −30 | 50 |
| 2.5 eq AlCl$_3$ | −30 | 50 |
| 2.5 eq FeCl$_3$ | −30 | 42 |
| 2.5 eq BiCl$_3$ | −30 | 18 |
| 2.5 eq ZnCl$_2$ | −30 | 38 |
| 2.5 eq MgCl$_2$ | −30 | 5 |
| 2.5 eq AlCl$_3$ + 0.5 eq pyridine | −30 | 70 |
| 2.5 eq FeCl$_3$ + 0.5 eq pyridine | −30 | 80 |
| 2.5 eq BiCl$_3$ + 0.5 eq pyridine | −30 | 5 |
| 2.5 eq ZnCl$_2$ + 0.5 eq pyridine | −30 | 21 |

EXAMPLE 5

The reaction, as detailed in the reaction scheme below, was carried out in the presence of dichloromethane solvent at 0° C.

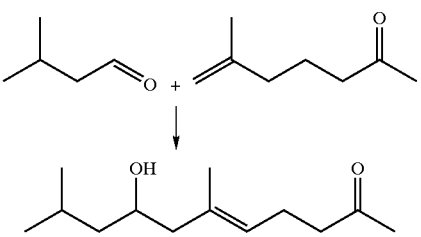

An equimolar mixture of the two reactants was added under an inert atmosphere to the reactor containing 2.5 mole equivalent of dichloro ethyl aluminium catalyst (in a solution of 1.8 M dichloromethane). The reaction was carried out for 2 hours at 0° C. in aqueous saturated sodium hydrogen carbonate. The resulting product was extracted with ether, washed with water and dried using magnesium sulphate, filtered and concentrated. The product was isolated by chromatography on silica gel or filtrated in crude solution after concentration of. The resulting product was extracted with ether, washed with water and dried using the solvent. A yield of 10% was obtained.

EXAMPLE 6

The procedure of Example 1 was repeated using the reactants as detailed in the reaction scheme below.

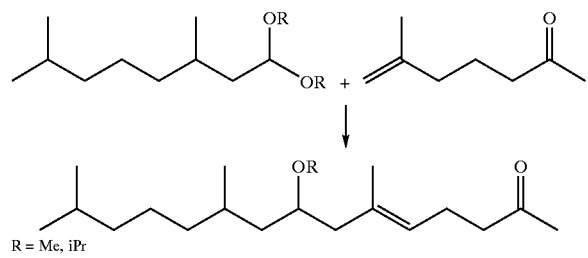

R = Me, iPr

The reaction conditions, catalysts used and the resulting yields are given in Table 4 below.

TABLE 4

| Nature of R Group | Catalyst and Amount | Temperature of Reaction (° C.) | Yield of Product (%) |
|---|---|---|---|
| methyl | 2.5 eq AlCl$_3$ | −30 | 60 |
| methyl | 2.5 eq AlCl$_3$ + 0.5 eq pyridine | −30 | 70 |
| isopropyl | 2.5 eq AlCl$_3$ + 0.5 eq pyridine | −30 | 40 |
| methyl | 2.5 eq FeCl$_3$ + 0.5 eq pyridine | −30 | 92 |

EXAMPLE 7

Hydrogenolysis of the product obtained in examples 4, 5 and 6 was carried out in the presence of a hydrogenolysis catalyst under experimental conditions as given in Table 5 below and as detailed in the reaction scheme below.

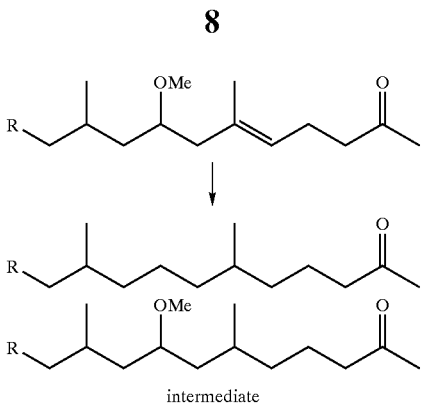

intermediate

R = Iso pentyl

The reactant and the catalyst were placed in an autoclave. The solvent was added. The autoclave was purged with argon prior to sealing. Hydrogen was then introduced into the autoclave to initiate the reaction. At the end of the reaction, the pressure was reduced to atmospheric pressure. The autoclave was then opened. The yield of product is shown in Table 5.

TABLE 5

| Solvent | Catalyst | H$_2$ Pressure (bar) | Conditions | Yield of Product |
|---|---|---|---|---|
| Acetic acid | 7% Pd/5%-C | 5 | 20° C., 6 hours | 30% phytone, 70% intermediate |
| Acetic acid | 5% Pd/10%-C | 50 | 100° C., 2 hours | 30% phytone, 70% intermediate |
| Acetic acid | 30% Pd/10%-C | 15 | 50° C., 5 hours | 30% phytone, 70% intermediate |
| toluene | 50% Pd/50% HCl | 1 | 20° C., 2 hours | 80% phytone, 20% intermediate |

EXAMPLE 8

Preparation of Vitamin E starting from 6-methyl 6-hepten 6-2-one, according to the following scheme:

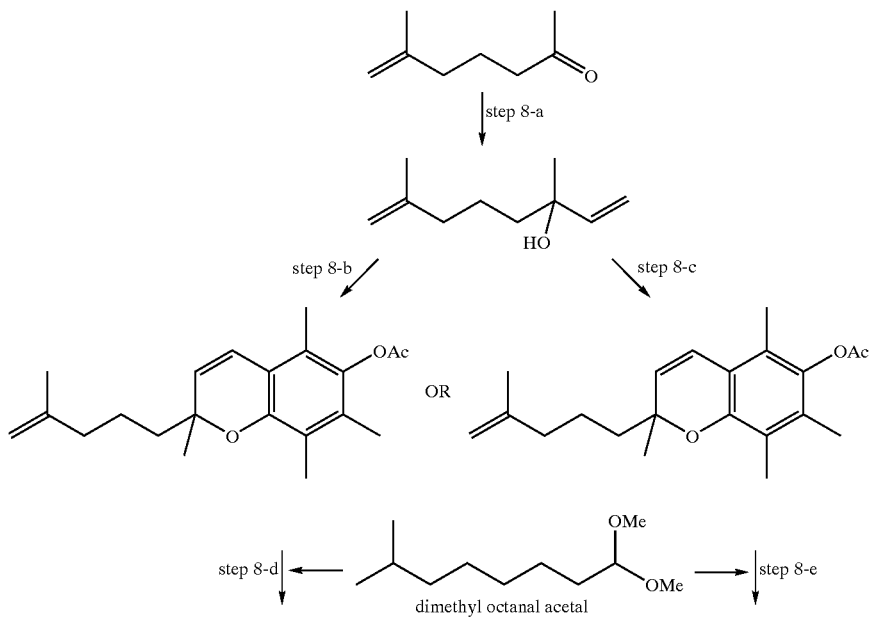

dimethyl octanal acetal

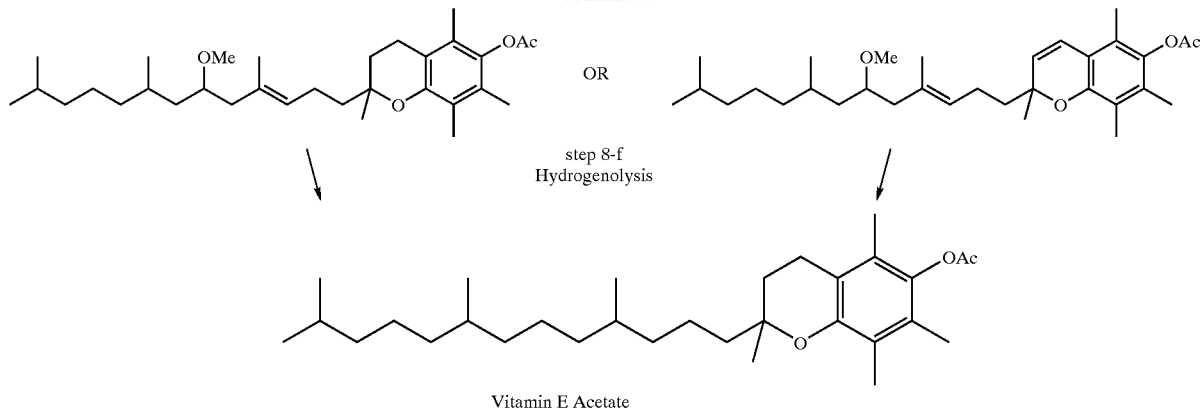

step 8-f
Hydrogenolysis

Vitamin E Acetate

Step (a): Preparation of Alpha-Linallol 24.7 ml of a 1.7 M solution of vinyl magnesium chloride in THF (42 mmols) was placed in a flask equipped with two necks, under argon. The solution was heated to 35° C., and 3.812 g (30 mmol) of 6-methyl 6heptene-2-one was introduced drop by drop to the magnesium compound over a period of 75 minutes. The mixture was then poured on to a mixture of 20 g of ice, 24 ml of water and 4 ml of 37% hydrochloric acid. The resulting organic phase was separated, dried over magnesium sulphate and concentrated. The yield was 4.563 g (98%) and 95% purity.

Step (b): Access to the Chromane 151 mg of trimethyl hydroquinone was dissolved, under argon, in 1 ml of ethyl acetate, and the solution was heated at 75° C. 16.24 mg of zinc chloride, 4 microliters of water, and 2 microliters of 37% hydrochloric acid were successively added. Alpha-linallol (154 mg) was added to the mixture in 30 mn. After 10 hours at 75° C., the alpha-linallol was consumed. 10 microlitres of 37% hydrochloric acid was added. Formation of the chromane was monitored on TLC plates. After 2 hours at 75° C., the mixture was cooled to 25° C., diluted with ether, washed by a normal solution of sodium hydroxyde, and with water, dried over magnesium sulphate, filtered and concentrated. The crude chromane, thus obtained, was diluted in 5 ml of triethyl amine, heated to reflux during five hours and cooled to 25° C. 204 mg of acetic anhydride was then added, and the mixture was kept at 25° C. 2 h under stirring. The mixture was concentrated under vacuum and the residue was chromatographed under silica gel. The desired acetylated chromane was isolated with a 60% yield (198 mg).

Step (c) Access to the Chromene 151 mg of trimethyl hydroquinone was dissolved under argon in 1 ml of ethyl acetate, and the solution was heated at 75° C. 16.24 mg of zinc chloride, 4 microliters of water, and 2 microliters of 37% hydrochloric acid were successively added. Alpha-linallol (154 mg) was added to the mixture over a period of 30 minutes. After 10 hours at 75° C., the mixture was cooled to 25° C., diluted with ether, washed by a normal solution of sodium hydroxyde, and with water, then dried over magnesium sulphate, filtered and concentrated. The crude benzoquinone adduct, thus obtained, was diluted in 5 ml of triethyl amine, heated to reflux during five hours and cooled to 25° C. 204 mg of acetic anhydride were added, and the mixture was kept at 25° C. for 2 hours under stirring. The mixture was concentrated under vacuum and the residue was chromatographed under silica gel. The desired acetylated chromene was isolated with a 50% yield (162 mg).

Step (d):

1 mmol of compound produced in step (b) and 1 mmol of dimethyl octanal dimethyl acetal were dissolved under inert atmosphere in 5 ml of dichloromethane. The catalyst (5% molar equivalents of scandium triflate or iron trichloride or ytterbium triflate) was added. The mixture was kept under stirring during 15 hours at ambient temperature. 3 ml of a saturated aqueous solution of sodium hydrogeno carbonate was added. The organic phase was separated, dried over magnesium sulphate, and concentrated in vacuo. The crude desired product was purified by column chromatography on silica gel (eluent: pentane/diethyl ether: 9/1 in volume).

Step (e):

1 mmol of compound produced in step (c) and 1 mmol of dimethyl octanal dimethyl acetal were dissolved under inert atmosphere in 5 ml of dichloromethane. The catalyst (5% molar equivalents of scandium triflate or iron trichloride or ytterbium triflate) was added. The mixture was kept under stirring during 15 hours at ambient temperature. 3 ml of a saturated aqueous solution of sodium hydrogeno carbonate was added. The organic phase was separated, dried over magnesium sulfate, and concentrated in vacuo. The crude desired product was purified by column chromatography on silica gel (eluent: pentane/diethyl ether: 9/1 in volume).

Step (f):

1 mmol of the product formed in steps (e) and (d), along with the catalyst (palladium 5% on charcoal; 5% weight equivalents), were placed in an autoclave. Diethyl ether (5 ml) was added. The autoclave was purged with argon prior to sealing. Hydrogen was then introduced (1 to 5 bars) into the autoclave to initiate the reaction. At the end of the reaction, the pressure was reduced to atmospheric pressure. The autoclave was then opened. Vitamin E was obtained after usual make-up of the mixture.

What is claimed is:

1. A process for the preparation of a compound of general formula (I)

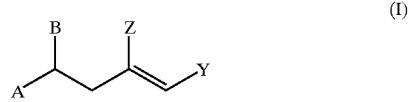

wherein A is a $C_1$ to $C_{20}$ hydrocarbon, Y and Z independently represent a $C_1$ to $C_{20}$ hydrocarbon which may contain an oxygenated functional group, B represents $OR^1$ or $NHR^1$ where $R^1$ is hydrogen or a $C_1$ to $C_6$ hydrocarbon, said process comprising reacting, in the presence of a Lewis acid catalyst, a compound of the general formula (II)

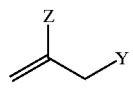
(II)

wherein Y and Z are as herein before defined, with a compound of the general formula (III) or a compound of general formula (IV)

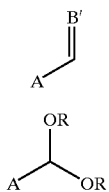
(III)

(IV)

wherein A is as hereinbefore defined, B' represents O or NR$^1$ where R$^1$ is as hereinbefore defined, and R is hydrogen or a C$_1$ to C$_6$ hydrocarbon.

2. A process as claimed in claim 1 in which Y is a C$_1$ to C$_{20}$ hydrocarbon with an oxygen group, Z is methyl, A is an aliphatic hydrocarbon and R is CH$_3$.

3. A process as claimed in claim 1 in which compounds of formula (II) are 6-methyl-6-heptene-2-one; 6-acetoxy 2,5,7,8-tetramethyl 2-[(4-methyl pent-4-ene)-1 yl]chromeme or 6-acetoxy 2,5,7,8-tetramethyl 2-[(4-methyl pent-4-ene)-1 yl]chromane.

4. A process as claimed in claim 1 in which compounds of formula (III) are 3 methyl butanal; imines of 3-methyl butanal; 3,6-dimethyl octanal; imines of 3,6-dimethyl octanal; citral and imines of citral.

5. A process as claimed in claim 1 in which compounds of formula (IV) are acetals of citral; acetals of 3-methyl butanal or acetals of 3,6-dimethyl octanal.

6. A process as claimed in claim 1 in which the Lewis acid is of general formula M(L)$_n$ where M represents aluminum, iron, magnesium, scandium, ytterium, zinc, titanium, silicium and bismuth; L represents a halide, CF$_3$SO$_3$, (CF$_3$SO$_2$)$_2$N, ClO$_4$ or a C$_1$ to C$_4$ alkyl, and n corresponds to the electronic valency of M, or is of general formula A–H wherein A represents CF$_3$SO$_3$ or (CF$_3$SO$_2$)$_2$N.

7. A process as claimed in claim 6 in which the Lewis acid is iron trichloride.

8. A process as claimed in claim 1 carried out in the presence of a base selected from aromatic amines, aliphatic amines and carbonate salts of Group I or II of the Periodic Table.

9. A process as claimed in claim 1 carried out in the presence of an organic solvent selected from chlorinated solvents, organic solvents, ether solvents, nitrile solvents and nitro solvents.

10. A process as claimed in claim 1 carried out at a temperature of from –80 to +150° C. and under atmospheric pressure.

11. A compound having the structure of one of the following structures compound V

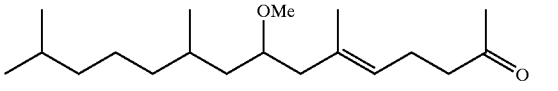

Compound VI

Compound VII

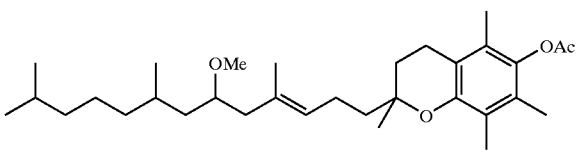

Compound VIII

12. A process for the preparation of phytone and/or Vitamin E which comprises hydrogenolysis of the compound of general formula (I) as defined in claim 1.

13. A process as claimed in claim 12 in which the hydrogenolysis is carried out in the presence of a catalyst which is a metal selected from palladium, platinum, nickel and zinc or a metal salt stannium chloride or molybdenum (III).

14. A process as claimed in claim 13 in which the hydrogenolysis is carried out in the presence of palladium on charcoal.

15. A process for the preparation of Vitamin E which comprises the hydrogenolysis of compound (VII) or (VIII) as defined in claim 11.

16. A process for the preparation of phytone which comprises hydrogenolysis of compound (V) or (VI) as defined in claim 11.

17. A process as claimed in claim 1, wherein Y and Z independently represent a C$_1$ to C$_{20}$ hydrocarbon.

18. A process as claimed in claim 6, wherein n is from 1 to 4.

19. A process as claimed in claim 1, wherein the Lewis acid catalyst is present in an amount of from 0.001 to 5 molar equivalents.

20. A process as claimed in claim 1, wherein the Lewis acid catalyst is present in an amount of from 0.02 to 2.5 molar equivalents.

21. A process as claimed in claim 1, wherein the mole ratio of the compound of general formula (II) to the compound of general formula (III) or the compound of general formula (IV) is from 0.2:1 to 5:1.

22. A process as claimed in claim 1, wherein the mole ratio of the compound of general formula (II) to the compound of general formula (III) or the compound of general formula (IV) is from 0.5:1 to 2:1.

23. A process as claimed in claim 1, said process being conducted at a temperature between –80 and 150° C.

24. A process as claimed in claim 1, said process being conducted at a temperature between –50 and 25° C.

25. A process as claimed in claim 1, said process being conducted at atmospheric pressure or higher.

26. A process as claimed in claim 1, wherein the compounds are reacted for 30 minutes to 24 hours.

* * * * *

UNITED STATES PATENT AND TRADEMARK OFFICE
CERTIFICATE OF CORRECTION

PATENT NO. : 6,867,307 B2
DATED : March 15, 2005
INVENTOR(S) : Jean-Erick Ancel et al.

It is certified that error appears in the above-identified patent and that said Letters Patent is hereby corrected as shown below:

<u>Title page,</u>
Item [30], Foreign Application Priortiy Data, change "0017200" to -- 00117200 --.

Signed and Sealed this

Twenty-fifth Day of April, 2006

JON W. DUDAS
*Director of the United States Patent and Trademark Office*